United States Patent
Stewart et al.

(10) Patent No.: US 11,491,468 B2
(45) Date of Patent: Nov. 8, 2022

(54) NOBLE METAL PROMOTED SUPPORTED INDIUM OXIDE CATALYST FOR THE HYDROGENATION OF $CO_2$ TO METHANOL AND PROCESS USING SAID CATALYST

(71) Applicants: TOTAL SE, Courbevoie (FR); ETH ZURICH, Zurich (CH)

(72) Inventors: Joseph Stewart, Uccle (BE); Daniel Curulla-Ferre, Uccle (BE); Javier Perez-Ramirez, Zürich (CH); Cecilia Mondelli, Zürich (CH); Matthias Frei, Zürich (CH)

(73) Assignees: TOTAL SE, Courbevoie (FR); ETH ZURICH, Zurich (CH)

( * ) Notice: Subject to any disclaimer, the term of this patent is extended or adjusted under 35 U.S.C. 154(b) by 0 days.

(21) Appl. No.: 17/272,872

(22) PCT Filed: Sep. 5, 2019

(86) PCT No.: PCT/EP2019/073660
§ 371 (c)(1),
(2) Date: Mar. 2, 2021

(87) PCT Pub. No.: WO2020/049081
PCT Pub. Date: Mar. 12, 2020

(65) Prior Publication Data
US 2021/0322957 A1    Oct. 21, 2021

(30) Foreign Application Priority Data

Sep. 6, 2018 (EP) .................................. 18306174
Sep. 6, 2018 (EP) .................................. 18306175

(51) Int. Cl.
*B01J 23/62* (2006.01)
*B01J 21/06* (2006.01)
(Continued)

(52) U.S. Cl.
CPC ............ *B01J 23/62* (2013.01); *B01J 6/001* (2013.01); *B01J 21/066* (2013.01); *B01J 23/08* (2013.01);
(Continued)

(58) Field of Classification Search
CPC .......... B01J 23/62; B01J 6/001; B01J 21/066; B01J 23/08; B01J 23/42; B01J 23/44;
(Continued)

(56) References Cited

U.S. PATENT DOCUMENTS 4,551,574 A   11/1985  Imai et al.
7,279,138 B2  10/2007  Pagani et al.
(Continued)

FOREIGN PATENT DOCUMENTS

CN   105498756 A   4/2016
CN   106390978 A   2/2017
(Continued)

OTHER PUBLICATIONS

Nobuhiro Iwasa et al., "New catalytic functions of Pd—Zn, Pd—Ga, Pd—In, Pt—Zn, Pt—Ga, and Pt—In alloys in the conversions of methanol." Catalysis Letters 54, pp. 119-123. (Year: 1998).*
(Continued)

*Primary Examiner* — Patricia L. Hailey
(74) *Attorney, Agent, or Firm* — Ewing & Jones, PLLC

(57) ABSTRACT

Supported catalyst for use in a process for the synthesis of methanol, characterized in that the supported catalyst comprises indium oxide in the form of $In_2O_3$ and at least one noble metal being palladium, Pd, wherein both indium oxide and at least one noble metal are deposited on a support remarkable in that the supported catalyst is a calcined supported catalyst comprising from 0.01 to 10.0 wt. % of palladium and zirconium dioxide ($ZrO_2$) in an amount of at least 50 wt. % on the total weight of said supported catalyst.

18 Claims, 3 Drawing Sheets

(51) Int. Cl.

| | |
|---|---|
| *B01J 23/08* | (2006.01) |
| *B01J 35/00* | (2006.01) |
| *B01J 35/10* | (2006.01) |
| *B01J 37/02* | (2006.01) |
| *B01J 37/03* | (2006.01) |
| *C07C 29/157* | (2006.01) |
| *B01J 6/00* | (2006.01) |
| *B01J 23/42* | (2006.01) |
| *B01J 23/44* | (2006.01) |
| *B01J 35/02* | (2006.01) |
| *C07C 1/04* | (2006.01) |

(52) U.S. Cl.
CPC .............. *B01J 23/42* (2013.01); *B01J 23/44* (2013.01); *B01J 35/006* (2013.01); *B01J 35/023* (2013.01); *B01J 35/1014* (2013.01); *B01J 35/1019* (2013.01); *B01J 37/0201* (2013.01); *B01J 37/031* (2013.01); *C07C 1/043* (2013.01); *C07C 1/046* (2013.01); *C07C 29/157* (2013.01)

(58) Field of Classification Search
CPC .... B01J 35/006; B01J 35/023; B01J 35/1014; B01J 35/1019; B01J 37/0201; B01J 37/031; C07C 1/043; C07C 1/046; C07C 29/157; C07C 29/151; C07C 29/153; C07C 31/04; C01P 2004/64; C10G 2/333; C10G 2/50
USPC .......................... 502/333, 339, 349; 568/840
See application file for complete search history.

(56) References Cited

U.S. PATENT DOCUMENTS

| | | | | |
|---|---|---|---|---|
| 11,278,872 | B2* | 3/2022 | Gascon | ................... B01J 35/08 |
| 2007/0238605 | A1* | 10/2007 | Strehlau | ................ B01J 23/626 502/79 |
| 2012/0207667 | A1* | 8/2012 | Men | .................... B01J 37/0219 502/332 |
| 2017/0239647 | A1 | 8/2017 | Lofficial et al. | |
| 2018/0362426 | A1* | 12/2018 | Chen | ................... B01J 23/8926 |
| 2020/0048173 | A1* | 2/2020 | Curulla-Ferre | ....... C07C 29/151 |
| 2020/0061582 | A1* | 2/2020 | Curulla-Ferre | ...... B01J 37/0201 |
| 2021/0178368 | A1* | 6/2021 | Gascon | ................... B01J 35/08 |
| 2021/0354114 | A1* | 11/2021 | Stewart | ............... B01J 35/1019 |

FOREIGN PATENT DOCUMENTS

| | | | | |
|---|---|---|---|---|
| CN | 105498756 | B | 5/2018 | |
| CN | 110052261 | * | 7/2019 | .............. B01J 23/08 |
| DE | 198 19 396 | A1 | 11/1999 | |
| DE | 10 2009 045804 | A1 | 4/2011 | |
| EP | 0208102 | A2 | 1/1987 | |
| EP | 2257366 | B1 | 7/2011 | |
| WO | 2017/118572 | A1 | 7/2017 | |

OTHER PUBLICATIONS

Roland L. Barbosa et al."Methanol Steam Reforming Over Indium-Promoted Pt/Al2O3 Catalyst : Nature of the Active Surface" Journal of Physical Chemistry C, vol. 117, 2013, pp. 6143-6150.
M.S. Frei et al., "Mechanism and microkinetics of methanol synthesis via CO2 hydrogenation on indium oxide", J. Catal., 2018, vol. 361, pp. 313-321.
S.E. Collins et al. "Hydrogen spillover in Ga2O3—Pd/SiO2 catalysts for methanol synthesis from CO2/H2"; Catal. Lett. 2005, vol. 103, pp. 83-88.
Xin Lin et al., "Remarkable support effect on the reactivity of Pt/In2O3/MOx catalysts for methanol steam reforming"; Journal of power sources, vol. 364, 2017, pp. 341-350.
International Search Report issued in Application No. PCT/EP2019/073660, dated Nov. 26, 2019; 4 pages.
Felix Studt et al. "Discovery of a Ni—Ga Catalyst for Carbon Dioxide Reduction to Methanol", Nature Chemistry, vol. 6, Apr. 2014 (320-324).
Jijie Wang et al. "A Highly Selective and Stable ZnO—ZrO2 Solid Solution Catalyst for CO2 Hydrogenation to Methanol", Science Advances, 2017; vol. 3: e1701290; 10 pages.
Tadahiro Fujitani et al. "Development of an Active Ga2O3 Supported Palladium Catalyst for the Synthesis of Methanol from Carbon Dioxide and Hydrogen", Applied Catalysis A: General, vol. 125 (1995) L199-L202.
Jingyun Ye et al. "Methanol Synthesis from CO2 Hydrogenation over a Pd4/In2O3 Model Catalyst: a Combined DFT and Kinetic Study", Journal of Catalysis, vol. 317 (2014) pp. 44-53.
Yong Men et al. "Methanol Stream Reforming Over Bimetallic Pd—In/Al2O3 Catalysts in a Microstructured Reactor" Applied Catalysis A: General, vol. 380 (2010) pp. 15-20.
Harald Lorenz et al. "Pd—In2O3 interaction due to Reduction in Hydrogen: Consequences for Methanol Stream Reforming", Applied Catalysis A: General, vol. 374 (2010) pp. 180-188.
Rui Ning et al."CO2 hydrogenation to methanol over Pd/In2O3 : effects of Pd/In2O3: effects of Pd and oxygen vacancy", Applied catalysis B: environmental, vol. 218, Jun. 23, 2017 pp. 488-497.
Xiao Jiang, et al. "Bimetallic Pd—Cu Catalysts for Selective CO2 Hydrogenation to Methanol", Applied Catalysis B: Environmental, vol. 170-171 (2015) pp. 173-185.
Antje Ota et al. "Comparative Study of Hydrotalcite-Derived Supported Pd2Ga and PdZn Intermetallic Nanoparticles as Methanol Synthesis and Methanol Steam Reforming Catalysts", Journal of catalysis, vol. 293 (2012) pp. 27-38.
Matthias Neumann et al. "Controlled Synthesis and Catalytic Properties of Supported In—Pd Intermetallic Compound", Journal of Catalysis, vol. 340 (2016) pp. 49-59.
Jingyun Ye et al. "Effect of PdIn Bimetallic Particle Formation on CO2 Reduction over the Pd—In/SiO2 Catalyst", Chemical Engineering Science, vol. 135 (2015) pp. 193-201.

* cited by examiner

NOBLE METAL PROMOTED SUPPORTED INDIUM OXIDE CATALYST FOR THE HYDROGENATION OF CO₂ TO METHANOL AND PROCESS USING SAID CATALYST

CROSS-REFERENCE TO RELATED APPLICATIONS

This application claims the benefit of PCT/EP2019/073660 filed Sep. 5, 2019, which claims priority from EP 18306174.6 filed Sep. 6, 2018 and EP 18306175.3 filed Sep. 6, 2018, which are incorporated herein by reference in their entireties for all purposes.

FIELD OF THE INVENTION

The invention relates to a process for the synthesis of methanol from $CO_2$-containing stream feeds. It also relates to the supported catalyst used in such a process.

BACKGROUND OF THE INVENTION

As part of the drive to tackle the growing global climate problem, it is attempted to reduce $CO_2$ levels. In order to reach the targets set out by the COP21 agreement, $CO_2$ emissions must be reduced by 50-85% by 2050. There are two main approaches, carbon capture and storage (CCS) and carbon capture and utilization (CCU), in which $CO_2$ is trapped, released in a controlled manner, and converted into products or intermediate building blocks.

Currently, there is much work on carbon capture technology and much debate on which technology will be the one to take off to be both financially and environmentally viable. No matter which technology emerges as the standout carbon capture process, the need to use this captured $CO_2$ as a lucrative $C_1$ source is undeniable. $CO_2$ utilization is a subject that has attracted a lot of attention over the past decade and beyond. Advances are not restricted to fine chemicals but they also apply to the incorporation of $CO_2$ into polymer structures, either as a monomer or as a precursor to a monomer.

Of particular interest is the synthesis of methanol. This chemical is a convenient liquid fuel and a raw material for synthetic hydrocarbons, which offers an alternative to depleting fossil fuels. Although it is currently industrialized by the conversion of $H_2$ and CO, methanol can be synthesized via the hydrogenation of $CO_2$. The conversion of $CO_2$ into methanol would allow a promising cycle, in which $CO_2$ can be converted to an energy storage compound, methanol, which can then be used giving $CO_2$ back, which can in turn be recaptured. Studies in this area are rapidly increasing, with the desire to find a stable, active, and selective catalyst for $CO_2$ conversion into methanol.

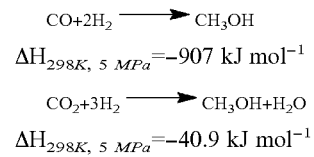

$$CO + 2H_2 \longrightarrow CH_3OH$$
$$\Delta H_{298K,\ 5\ MPa} = -907\ kJ\ mol^{-1}$$

$$CO_2 + 3H_2 \longrightarrow CH_3OH + H_2O$$
$$\Delta H_{298K,\ 5\ MPa} = -40.9\ kJ\ mol^{-1}$$

Several catalysts have been proposed and studied to perform methanol synthesis from $CO_2$. For example, Felix Studt et al. in "*Discovery of a Ni—Ga Catalyst for Carbon Dioxide Reduction to Methanol*", Nature Chemistry, Vol. 6, April 2014 (320-324), describes the use of a Ni—Ga catalyst that reduces $CO_2$ to methanol at ambient pressure.

More recently, WO2017/118572 describes an indium-based catalytic system and a process for methanol synthesis from a $CO_2$-containing syngas. The catalyst introduced is an indium oxide supported on zirconia system that exhibits 100% selectivity towards methanol, good stability up to 1000 h in the presence of $CO_2$ as the sole carbon source and high activity. The stability of the catalyst was particularly interesting since when it was benchmarked against a conventional Cu-based methanol synthesis catalyst, the Cu-based catalyst showed significant loss of activity (loss of 44% activity within 100 h) due to the co-production of water when converting $CO_2$.

The effect of zirconium dioxide as a catalyst was also studied in "*A Highly Selective and Stable ZnO-ZrO₂ Solid Solution Catalyst for CO₂ Hydrogenation to Methanol*", Jijie Wang et al. Science Advances, 2017; 3: e1701290. The methanol selectivity achieved was of up to 86-91% with a $CO_2$ single-pass conversion of more than 10% under the reported reaction conditions. Zr and Zn showed a synergetic effect and the ZnO—ZrO₂ catalyst demonstrated a high stability for at least 500 h on stream. In addition, it did not deactivate in the presence of 50 ppm of $SO_2$ or $H_2S$.

CN106390978 reports catalysts for synthesis of methanol through carbon dioxide hydrogenation. The catalysts are produced by co-precipitation of two metal oxides. In particular, the ZnO—ZrO₂ catalyst was found to have a methanol selectivity of 80%.

Palladium-based catalysts have also been considered for a long time. In 1995, Tadahiro Fujitani et al. in "*Development of an Active Ga₂O₃ Supported Palladium Catalyst for the Synthesis of Methanol from Carbon Dioxide and Hydrogen*", Applied Catalysis A: General 125 (1995) L199-L200, already came to the conclusion that there was a significant effect of the support on the catalytic activity of palladium-based catalysts for methanol synthesis from carbon dioxide and hydrogen.

Jingyun Ye et al. in "*Methanol Synthesis from CO₂ Hydrogenation over a Pd₄/In₂O₃ Model Catalyst: a Combined DFT and Kinetic Study*", Journal of Catalysis 317 (2014) 44-53, have examined three possible routes in the reaction network to produce methanol and water. The density functional theory (DFT) results showed that the HCOO route competes with the reverse water-gas shift (RWGS) route.

Yong Men et al. in "*Methanol Stream Reforming Over Bimetallic Pd—In/Al₂O₃ Catalysts in a Microstructured Reactor*"; Applied Catalysis A: General 380 (2010) 15-20, describe the use of bimetallic PdIn catalysts. The catalytic activity and $CO_2$ selectivity were found to be markedly dependent on the Pd:In ratio as well as on the metal loading. The high $CO_2$ selectivity of Pd—In/Al₂O₃ catalysts has been ascribed to the Pd—In alloy formation, whereas the metallic Pd without contact with indium is responsible for CO selectivity.

The Pd—In₂O₃ interaction and their effect on the catalytic activity were further studied. Harald Lorenz et al. in "*Pd—In₂O₃ interaction due to Reduction in Hydrogen: Consequences for Methanol Stream Reforming*", Applied Catalysis A: General 374 (2010) 180-188, showed that oxidative treatments of the bimetallic PdIn catalysts led to the decomposition of PdIn and the formation of an In₂O₃ shell covering the Pd particles.

More recently, Pd—In catalysts wherein the formation of Pd—In bimetallic species was avoided have also been produced and tested. "*CO₂ Hydrogenation to Methanol over Pd/In₂O₃; effects of Pd and Oxygen Vacancy*"; Ning Riu et al. Applied Catalysis B: Environmental, 218 (2017) 488-497 reports the results of these experiments. The formation of Pd—In bimetallic species was found to reduce the methanol yield. Thus, a new catalyst consists of $In_2O_3$ highly-dispersed Pd-nanoparticles predominately exposing the (111) faces with an average particle size of 3.6 nm. The catalysts tested showed superior performances for $CO_2$ hydrogenation to methanol with a $CO_2$ conversion over 20% and methanol selectivity over 70%, corresponding to a space-time yield (STY) up to 0.89 $g_{MeOH}$ $h^{-1}$ $g_{CAT}^{-1}$ at 300° C. and 5 MPa.

Pd—Cu catalysts were also studied. Xiao Jiang et al. in "*Bimetallic Pd—Cu Catalysts for Selective $CO_2$ Hydrogenation to Methanol*", Applied Catalysis B: Environmental 170-171 (2015) 173-185, reported a strong synergetic effect on promoting methanol formation over amorphous silica supported Pd—Cu bimetallic catalysts when the Pd/(Pd+Cu) atomic ratios lied in the range of 0.25 to 0.34.

Antje Ota et al. in "*Comparative Study of Hydrotalcite-Derived Supported $Pd_2Ga$ and PdZn intermetallic nanoparticles as methanol synthesis and methanol Steam Reforming Catalysts*" Journal of catalysis 293 (2012) 27-38, described an improved selectivity to $CO_2$ and to methanol for catalysts comprising Zn or Ga.

Matthias Neumann et al. in "*Controlled Synthesis and Catalytic Properties of Supported In—Pd Intermetallic Compound*", Journal of Catalysis 340 (2016) 49-59, described the formation of different intermetallic In—Pd by reduction of $PdO/In_2O_3$ with hydrogen. The materials produced exhibited catalytic activity for methanol steam reforming and high $CO_2$ selectivities of up to 98%. Long term measurements proved the superior stability of the In—Pd/$In_2O_3$ materials in comparison to Cu-based systems over 100 h on stream with high selectivity.

Jingyun Ye et al. in "*Effect of PdIn Bimetallic Particle Formation on $CO_2$ Reduction over the Pd—In/$SiO_2$ Catalyst*", Chemical Engineering Science 135 (2015) 193-201, discover that Pd—In/$SiO_2$ catalysts showed 100% selectivity toward CO and no detectacle $CH_4$ formation. This selectivity to CO was found to be a result of the formation of bimetallic Pd—In species.

Roland L. Barbosa et al. "Methanol steam reforming over Indium-promoted Pt/Al2O3 catalyst: Nature of the active surface" Journal of Physical Chemistry C, Vol. 117, No 12, 28 Mar. 2013 described the methanol steam reforming over a catalyst prepared via impregnation of In and Pt on a Al2O3 support.

Liu Xin et al. «Remarkable support effect on the reactivity of Pt/In2O3/Mox catalysts for methanol steam reforming» Journal of power sources, Vol. 364, 19 Aug. 2017, pages 341-350 described the methanol steam reforming with a catalyst containing Pt and In2O3 deposited on various supports: Al2O3, MgO, Fe2O3, MgO, La2O3, and CeO2.

US 2017/239647 described semi conductor such as In2O3/Pt/TiO2 prepared via subsequent impregnation of Pt and of In2O3.

DE 10 2009 045804 A1 described the steam reforming of methanol on catalyst prepared on a metallic oxide catalyst containing In2O3 as well as at least one element selected from Pd, Pt, Rh and Ir and an alloy of In with as at least one element selected from Pd, Pt, Rh and Ir.

DE 198 19 396 A1 described the selective hydrogenation of unsaturated aldehydes to the corresponding alcohols on a catalyst containing silver and indium deposited on a support.

U.S. Pat. No. 4,551,574 described a catalyst composition comprising platinum, tin, indium component, an alkali or alkaline earth component and a porous support material. The catalyst is used to dehydrogenate C10-C15 paraffines into the corresponding normal olefins.

Rui Ning et al. "CO2 hydrogenation to methanol over Pd/In2O3:effects of Pd/In2O3: effects of Pd and oxygen vacancy", Applied catalysis B: environmental Vol 218, 23 Jun. 2017 pages 488-497 described the conversion of CO2 into methanol over a catalyst constituted of Pd deposited on In2O3 as support.

Thus, there is still a need to find a new catalyst and a new process for the conversion of $CO_2$ into methanol.

SUMMARY OF THE INVENTION

The present invention provides the solution to one or more of the aforementioned needs. It is an object of the invention to provide a new process and a new supported catalyst for methanol synthesis from $CO_2$. Another object of the invention is to provide a new process and a new supported catalyst allowing improvements in $CO_2$ conversion into methanol. Another object of the invention is to provide a supported catalyst and a process for methanol synthesis showing improvements in $CO_2$ conversion to methanol, together with high space-time yield and high selectivity to methanol. Another object of the invention is to provide a supported catalyst and a process for methanol synthesis showing high stability of the supported catalyst.

According to a first aspect, the invention provides a supported catalyst for use in a process for the synthesis of methanol, wherein the supported catalyst comprises indium oxide in the form of In2O3 and at least one noble metal being palladium, Pd, wherein both indium oxide and the at least one noble metal are deposited on a support remarkable in that the supported catalyst is a calcined supported catalyst comprising from 0.01 to 10.0 wt. % of palladium and zirconium dioxide (ZrO2) in an amount of at least 50 wt. % on the total weight of said supported catalyst.

Indeed, it has been found by the inventors that the presence of noble metal, being palladium, in a supported indium catalyst allows to increase the space time yield (STY) showed by the supported catalyst in a process for the synthesis of methanol as compared to a supported indium catalyst that is not noble metal promoted.

With preference, one or more of the following features can be used to better define the inventive catalyst:
- The supported catalyst is a calcined catalyst and shows a crystalline structure as determined by XRD.
- The supported catalyst is a calcined catalyst and comprises from 0.01 to 7.0 wt. %, of the at least one noble metal based on the total weight of the calcined catalyst, more preferably from 0.05 to 5.0 wt. %; even more preferably from 0.1 to 2.0 wt. %; and most preferably from 0.5 to 1.0 wt. %.
- The average particle size of the noble metal phase is less than 5 nm, preferably less than 4 nm, more preferably less than 2 nm as determined by STEM-EDX.
- The average crystal size of $In_2O_3$ is less than 20 nm, as determined by XRD, preferably less than 15 nm, more preferably less than 12 nm, and even more preferably less than 10 nm.
- The supported catalyst is a calcined supported catalyst and the support comprises zirconium dioxide ($ZrO_2$) in an amount of at least 80 wt. %, and even more preferably at least 90 wt. % based on the total weight of the calcined supported catalyst.
- The support comprises zirconium dioxide ($ZrO_2$), the zirconium dioxide can be monoclinic, tetragonal, or cubic.
- The supported catalyst is a calcined supported catalyst and the indium oxide content in the form of $In_2O_3$ is ranging from 1 to 20% by weight, preferably from 5 to 15 wt. % based on the total weight of said supported catalyst.

The supported catalyst is a calcined supported catalyst and has preferably a surface area in the range of about 5 m² g⁻¹ to about 400 m² g⁻¹, such as from 30 m² g⁻¹ to about 200 m² g⁻¹ as determined according to $N_2$ sorption analysis according to ASTM D3663-03.

According to a second aspect, the invention provides a method to prepare a supported catalyst according to the first aspect, wherein the supported catalyst is prepared by impregnation or by deposition precipitation. Preferably, impregnation is a wet impregnation.

With preference, the supported catalyst is a calcined catalyst, namely a catalyst with a crystalline structure, and in that the method comprises a step of calcination of the supported catalyst performed at a temperature of at least 473 K (199.85° C.), with preference of at least 573 K (299.85° C.).

According to a third aspect, the invention provides a process for methanol synthesis comprising the following steps:
providing a feed stream comprising hydrogen and carbon oxides selected from carbon dioxide or a mixture of carbon dioxide and carbon monoxide, wherein carbon dioxide represents from 1 to 50 mol % of the total molar content of the feed stream, carbon monoxide is contained from 0 to 85 mol % of the total molar content, and $H_2$ is from 5 to 99 mol % of the total molar content of the feed stream;
providing a catalyst according to the first aspect of the invention and/or prepared by the method according to the second aspect of the invention;
putting in contact said feed stream with said catalyst at a reaction temperature of at least 373 K (99.85° C.) and under a pressure of at least 0.5 MPa; and
recovering the methanol from the effluents by a separation process.

With preference, one or more of the following features can be used to better define the inventive process:
The reaction temperature is at least 463 K (189.85° C.), preferably at least 523 K (249.85° C.), more preferably at least 553 K (279.85° C.).
The reaction temperature is at most 773 K (499.85° C.).
The reaction pressure is at least 1 MPa, preferably at least 2 MPa, more preferably at least 3 MPa, even more preferably at least 4 MPa, most preferably at least 5 MPa.
The reaction pressure is at most 50 MPa, preferably at most 25 MPa, more preferably at most 10 MPa.
The feed stream comprises at least 3 mol % of $CO_2$ based on the total molar content of the feed stream, preferably at least 5 mol %, more preferably at least 10 mol %, even more preferably at least 20 mol %. The feed comprises at most 40 mol % of $CO_2$ based on the total molar content of the feed stream, preferably at most 35 mol %, more preferably at most 30 mol %.
The feed stream comprises preferably at least 1 mol % of CO based on the total molar content of the feed stream, preferably at least 2 mol %, more preferably at least 10 mol %.
The feed stream comprises at most 75 mol % of CO based on the total molar content of the feed stream, preferably at most 65 mol %, more preferably at most 50 mol %.
The feed stream comprises at least 10 mol % of $H_2$ based on the total molar content of the feed stream, preferably at least 20 mol %, more preferably at least 30 mol %.
The feed stream comprises at most 90 mol % of $H_2$ based on the total molar content of the feed stream, preferably at most 80 mol %, more preferably at most 70 mol %, even more preferably at most 60 mol %.
The feed stream comprises a mixture of carbon dioxide and carbon monoxide and the feed stream contains at most 30 mol % of $CO_2$ based on the total molar content of the carbon oxide, or the feed stream comprises a mixture of carbon dioxide and carbon monoxide and the feed stream contains more than 30 mol % of $CO_2$ based on the total molar content of the carbon oxide.
The molar ratio of hydrogen to carbon dioxide ($H_2:CO_2$) in the feed stream is at least 1:1, preferably it is at least 3:1, and more preferably it is at least 4:1.
The feed stream is put in contact with the supported catalyst at a weight hourly space velocity (WHSV) ranging from 1,000 to 60,000 $cm^3_{STP} g_{cat} h^{-1}$; preferably of at least 16,000 $cm^3_{STP} g_{cat} h^{-1}$, more preferably of at least 24,000 $cm^3_{STP} g_{cat} h^{-1}$, and even more preferably of at least 48,000 $cm^3_{STP} g_{cat} h^{-1}$.
The process is carried out during more than 100 h, preferably more than 300 h, more preferably more than 1000 h, without the need of replacement or reactivation of the supported catalyst.

According to a fourth aspect, the invention provides the use of a catalyst according to the first aspect of the invention in a process of hydrogenation of $CO_2$ to methanol.

DETAILED DESCRIPTION OF THE INVENTION

Figure 1:
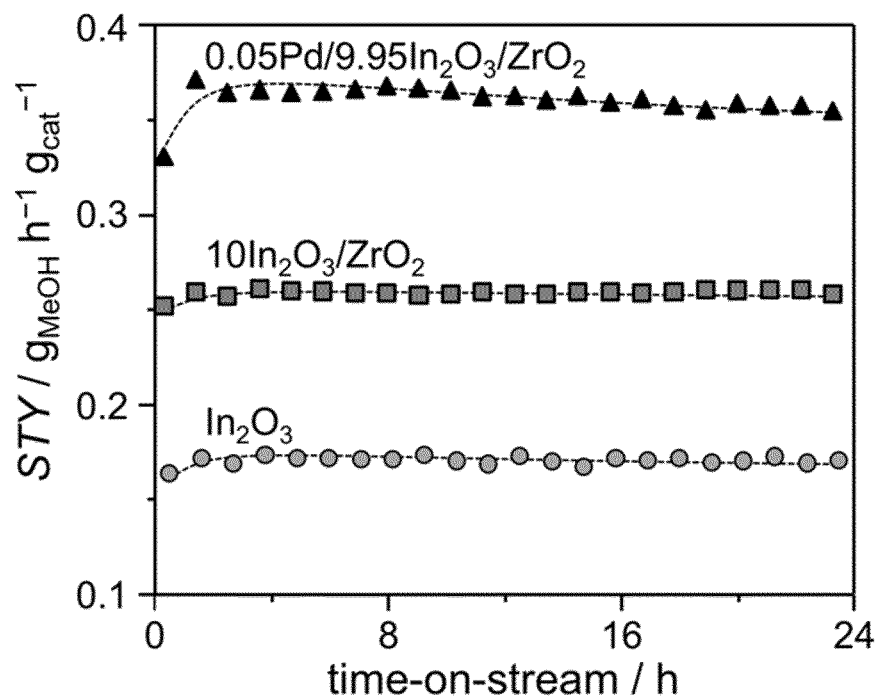
FIG. 1 depicts the STY of methanol over indium oxide, 10 wt. % indium oxide on zirconia, and 0.05 wt. % palladium and 9.95 wt. % indium oxide on zirconia over a 24-h period. Conditions: WHSV=24,000, molar $H_2:CO_2$=4, 5.0 MPa, 553 K, catalyst prepared via wet impregnation.

As used herein the generic term "catalyst" refers to both a "bulk" and a "supported catalyst". A bulk catalyst is a catalyst containing only the main active phase (i.e., indium oxide). A supported catalyst comprises the bulk catalyst and a support (e.g., $ZrO_2$). A noble metal promoted catalyst is a catalyst in which a noble metal has been added.

A co-precipitated catalyst is a catalyst wherein the active phase is intimately mixed with the support, in contrast with deposition precipitation techniques and impregnation techniques wherein the active phase is deposited on the support.

According to the invention, a supported catalyst comprises a catalyst and a support to provide mechanical support to the supported catalyst as well as to further enhance exposure of a feed stream to active sites of the supported catalyst.

In methanol synthesis according to the invention, a feed gas composed of hydrogen gas and carbon oxides ($CO_2$ alone or a mixture of $CO_2$ and CO gases) are caused to interact on a ternary catalyst comprising indium oxide, a noble metal and a support.

Catalyst and Preparation of the Supported Catalyst

The present invention contemplates the use of a supported catalyst in a process for the synthesis of methanol wherein, the supported catalyst comprises indium oxide in the form of $In_2O_3$ and at least one noble metal, wherein both indium oxide and the at least one noble metal are deposited on a support.

The catalyst comprises both indium oxide in the form of $In_2O_3$ and an additional metal selected from noble metals, being palladium. The amount of the catalyst (represented as weight loading of the catalyst based on the total weight of the calcined supported catalyst) can be in the range of about 0.1-95 wt. %.

The supported catalyst is a calcined catalyst. This feature can be evidenced by the crystalline structure of indium oxide observed in the X-ray diffraction and/or the absence of organic and/or nitrogen compounds in HCN analysis, that would be derived from the metal precursors, e.g., In $(NO_3)_3 \cdot xH_2O$. Indeed, the non-calcined catalyst would exhibit organic and/or nitrous and/or hydrogen content in its HCN analysis.

In a preferred embodiment, the average size of the noble metal phase is less than 5 nm as determined by STEM-EDX, preferably less than 4 nm, more preferably less than 2 nm.

In an embodiment, the supported catalyst is a calcined supported catalyst and comprises from 0.01 to 10 wt. % of the at least one noble metal based on the total weight of the calcined supported catalyst.

The supported catalyst is a calcined supported catalyst and comprises at least 0.05 wt. % of the at least one noble metal based on the total weight of the calcined supported catalyst, preferably at least 0.1 wt. %, more preferably at least 0.3 wt. %, even more preferably at least 0.5 wt. %, and most preferably at least 0.7 wt. %.

The supported catalyst is a calcined supported catalyst and comprises at most 10.0 wt. % of the at least one noble metal based on the total weight of the calcined supported catalyst, preferably at most 7.0 wt. %, more preferably at most 5.0 wt. %, even more preferably at most 2.0 wt. %, and most preferably at most 1.0 wt. %.

In an embodiment, the supported catalyst is a calcined supported catalyst and the indium oxide content in the form of $In_2O_3$ of the supported catalyst, is at most 70 wt. %, preferably at most 60 wt. %, preferably of at most 50 wt. %, more preferably of at most 40 wt. %, even more preferably of at most 30 wt. %, most preferably of at most 20 wt. %, and even most preferably of at most 14 wt. % based to the total weight of the calcined supported catalyst.

In an embodiment, the supported catalyst is a calcined supported catalyst and the indium oxide content in the form of $In_2O_3$ of the supported catalyst, is at least 1 wt. %, preferably at least 5 wt. %, more preferably at least 8 wt. % based to the total weight of the calcined supported catalyst.

With the support being zirconium dioxide ($ZrO_2$), the zirconium dioxide can be monoclinic, tetragonal, or cubic.

The supported catalyst is a calcined supported catalyst and the support comprises zirconium dioxide ($ZrO_2$) in an amount of at least 50 wt. %, even more preferably at least 80 wt. %, and most preferably at least 90 wt. % based on the total weight of the calcined supported catalyst.

In an embodiment, the support is zirconium dioxide or a combination of zirconium dioxide with another support in which zirconium dioxide is contained in an amount of at least 50 wt. %, more preferably at least 80 wt. %, and even more preferably at least 90 wt. % based on the total weight of the support, the other support being selected from silica ($SiO_2$), alumina ($Al_2O_3$), gallium oxide ($Ga_2O_3$), cerium oxide (CeO2), vanadium oxide ($V_2O_5$), chromium oxide ($Cr_2O_3$), titanium dioxide ($TiO_2$), magnesium oxide (MgO), zinc oxide (ZnO), tin oxide ($SnO_2$), carbon (C), and combinations thereof; preferably the other support is selected from zinc oxide (ZnO), titanium dioxide ($TiO_2$), and combinations thereof.

A catalyst support can be porous or non-porous. In some embodiments, a catalyst support can be provided in a particulate form of particles having a surface area (i.e., BET surface area) as determined by $N_2$ sorption analysis according to ASTM D3663-03, in the range of about 5 $m^2$ $g^{-1}$ to about 400 $m^2$ $g^{-1}$, such as from 30 $m^2$ $g^{-1}$ to about 200 $m^2$ $g^{-1}$ as determined according to $N_2$ sorption analysis, a pore volume in the range of about 0.1 $cm^3/g$ to about 10 $cm^3$ $g^{-1}$, such as from about 0.2 $cm^3$ $g^{-1}$ to about 5 $cm^3$ $g^{-1}$.

The calcined supported catalyst has preferably a surface area (i.e., BET surface area) as determined by $N_2$ sorption analysis according to ASTM D3663-03, in the range of about 5 $m^2$ $g^{-1}$ to about 400 $m^2$ $g^{-1}$, such as from 30 $m^2$ $g^{-1}$ to about 200 $m^2$ $g^{-1}$.

The catalyst can be combined with a catalyst support or other support medium through, for example impregnation, such that the catalyst can be coated on, deposited on, impregnated on or otherwise disposed adjacent to the catalyst support. For example, a supported catalyst can be synthesized by an impregnation step followed by a calcination step. The catalyst can be provided in technical shapes such as extrudates, granules, spheres, monoliths, or pellets and might contain additives such as lubricants, peptizers, plasticizers, porogens, binders, and/or fillers.

In a preferred embodiment the calcination step is performed at a temperature above 500 K (226.85° C.), preferably above 530 K (256.85° C.), more preferably above 550 K (276.85° C.), even more preferably above 570 K (296.85° C.).

The above catalyst is useful for the synthesis of methanol from hydrogen and carbon oxides or the reverse reaction thereof.

Hydrogenation of Carbon Dioxide to Methanol

In methanol synthesis according to the invention, a feed gas composed of hydrogen gas and carbon oxides ($CO_2$ alone or a mixture of $CO_2$ and CO gases) are caused to interact on an indium oxide-based catalyst.

The invention provides a process for methanol synthesis comprising the following steps:
  providing a feed stream comprising hydrogen and carbon oxides selected from carbon dioxide or a mixture of carbon dioxide and carbon monoxide, wherein carbon dioxide represents from 1 to 50 mol % of the total molar content of the feed stream, carbon monoxide is contained from 0 to 85 mol % of the total molar content, and $H_2$ is comprised from 5 to 99 mol % of the total molar content of the feed stream;
  providing a supported catalyst comprises indium oxide in the form of $In_2O_3$ and at least one noble metal, wherein both indium oxide and the at least one noble metal are deposited on a support;
  putting in contact said feed stream with said catalyst at a reaction temperature of at least 373 K (99.85° C.) and under a pressure of at least 0.5 MPa; and
  recovering the methanol from the effluents by a separation process.

The process can be carried out in a gaseous phase or in a liquid phase. The solvent that can be used for the reaction in liquid phase includes hydrocarbons and other solvents which are preferably insoluble or only sparingly soluble in water. Preferably, the process is carried out in a gaseous phase.

Prior to reaction the supported catalyst is activated in situ by raising the temperature to at least 553 K in a flow of a gas feed stream for activation selected from inert gases, hydrogen, carbon monoxide, carbon dioxide, or a mixture thereof, preferably the gas feed stream for activation is or comprises an inert gas, more preferably the gas feed stream for activation is or comprises nitrogen.

The process is carried out in a reactor comprising:
lines to introduce a feed stream to the reactor and remove products from the reactor;
a device for heating the reactor;
a temperature sensor and controller for detecting and controlling the temperature of the reactor at a reaction temperature chosen between 373 K (99.85° C.) and 673 K (399.85° C.);
flow controllers to control the rate of the feed stream to the reactor; and
a pressure controller to control the reactor pressure in order to set it at a pressure of at least 0.5 MPa.

In accordance to the invention, the feed stream comprises hydrogen and carbon oxides selected from carbon dioxide ($CO_2$) or a mixture of carbon dioxide and carbon monoxide.

However, in a preferred embodiment, the feed stream comprises hydrogen and carbon dioxide.

When the feed stream comprises hydrogen and a mixture of carbon dioxide and carbon monoxide, the feed stream can be CO-rich or $CO_2$-rich. In accordance to the invention, $CO_2$-rich feed stream contains more than 30 mol % of $CO_2$ based on the total molar content of the carbon oxide. In a preferred embodiment of the invention, the feed stream is $CO_2$-rich.

The feed stream comprises $CO_2$ and $H_2$, or $H_2$ and a mixture of $CO_2$ and CO, preferably the feed stream may also comprise a further gaseous component such as an inert gas. The inert gas is for example nitrogen.

In a preferred embodiment, the molar ratio of hydrogen to carbon dioxide in the feed stream is at least 1:1, preferably at least 3:1, more preferably at least 4:1, even more preferably at least 6:1; and/or the molar ratio of hydrogen to carbon dioxide in the feed stream is at most 50:1, preferably at most 25:1.

In a preferred embodiment, the feed stream contains hydrogen and carbon oxides selected from carbon dioxide or a mixture of carbon dioxide and carbon monoxide and the feed stream comprises at least 10 mol % of $H_2$ based on the total molar content of the feed stream, preferably at least 20 mol %, more preferably at least 30 mol %.

In a preferred embodiment the feed stream contains hydrogen and carbon oxides selected from carbon dioxide or a mixture of carbon dioxide and carbon monoxide and the feed stream comprises at most 99 mol % of $H_2$ based on the total molar content of the feed stream, preferably at most 90 mol %, more preferably at most 80 mol %, even more preferably at most 70 mol %, and most preferably at most 60 mol %.

In a preferred embodiment, the process is carried out at a reaction temperature of at least 473 K (199.85° C.), preferably of at least 523 K (249.85° C.), more preferably of at least 553 K (279.85° C.).

In another preferred embodiment, the pressure is at least 1 MPa, preferably at least 2 MPa, more preferably at least 3 MPa, even more preferably at least 4 MPa and most preferably at least 5 MPa.

In a preferred embodiment, the weight hourly space velocity (WHSV) is in the range of 1,000 to 100,000 cubic centimeters at standard temperature and pressure (STP) of reactant gases per gram of catalyst charged to the reactor per hour, preferably 2,000 to 70,000 $cm^3_{STP}\ g_{cat}^{-1}\ h^{-1}$, more preferably 5,000 to 60,000 $cm^3_{STP}\ g_{cat}^{-1}\ h^{-1}$, and more preferably 15,000 to 50,000 $cm^3_{STP}\ g_{cat}^{-1}\ h^{-1}$.

In a preferred embodiment the process can be carried out with a stable performance with respect to activity and selectivity during more than 100 h, preferably more than 300 h, more preferably more than 1000 h, without the need of reactivation or replacement of the supported catalyst.

In an embodiment, the process is carried out in a fixed-bed or in a fluidized-bed reactor comprising at least one catalytic bed. Such reactors are well-known from the person skilled in the art and for instance described in EP2257366 or in U.S. Pat. No. 7,279,138.

Test Methods and Definitions

Activity for methanol synthesis reaction is determined using a home-made fixed-bed reactor set-up, which has been described in detail previously (M. S. Frei et al. *J. Catal.*, 2018, 361, 313-321). Briefly, it comprises a high-pressure continuous-flow fixed-bed reactor with an inner diameter of 2.1 mm surrounded by an electric furnace. The reactor was loaded with 100 mg of catalyst with a particle size of 100-125 μm, which was held in place by a bed of quartz wool and was heated from ambient temperature to 553 K (5 K $min^{-1}$) at 5 MPa under a He flow of 20 $cm^3_{STP}\ g_{cat}\ min^{-1}$. After 3 h, the gas flow was switched to the reactant mixture (40 $cm^3_{STP}\ min^{-1}$) comprising $H_2$ and $CO_2$ (Messer, 99.997% and 99.999%, respectively) in a molar ratio of 4:1. A constant flow (2.5 $cm^3_{STP}\ min^{-1}$) of 20 mol % $CH_4$ in He (Messer, both 99.999%) was added to the effluent stream to serve as an internal standard. The effluent stream was sampled every 12 min and analyzed by an online gas chromatograph (GC, Agilent 7890A), equipped with two parallel columns (Agilent GS Gaspro and Agilent DB-1) connected to a flame ionization detector (FID) and a thermal conductivity detector (TCD), to determine the mol % content of the reactants $H_2$, $CO_2$, and CO in the feed stream and the mol % content of the reactants and the methanol product in the outlet stream.

For each compound i, the response factor $F_i$ respective to the internal standard ($CH_4$) was calculated by the following equation:

$$F_i = \frac{A_i / \dot{n}_i^{in}}{A_{CH_4} / \dot{n}_{CH_4}^{in}}$$

where $A_i$ is the integrated area determined for compound i by the GC and $\dot{n}_i^{in}$ corresponds to its known adjusted molar flowrate. Each response factor was calculated as the average of 5 calibration points around the expected concentration of the respective analyte i.

Upon reaction the unknown effluent molar flowrate $\dot{n}_i^{out}$ was determined by the following equation:

$$\dot{n}_i^{out} = \frac{A_i \times F_i}{A_{CH_4}} \times \dot{n}_{CH_4}^{in}$$

$CO_2$ conversion ($X_{CO2}$), methanol selectivity ($S_{MeOH}$) and yield ($Y_{MeOH}$) in percent and methanol space-time yield ($STY_{MeOH}$) were calculated applying the following equations:

$$X_{CO_2} = \frac{\dot{n}^{in}_{CO_2} - \dot{n}^{out}_{CO_2}}{\dot{n}^{in}_{CO_2}} \times 100$$

$$S_{MeOH} = \frac{\dot{n}^{in}_{MeOH} - \dot{n}^{out}_{MeOH}}{\dot{n}^{in}_{CO_2} - \dot{n}^{out}_{CO_2}} \times 100$$

$$Y_{MeOH} = X_{CO_2} \times S_{MeOH}$$

$$STY_{MeOH} = \frac{\dot{n}^{in}_{MeOH} - \dot{n}^{out}_{MeOH}}{W_{cat}} \times M_{MeOH}$$

where $W_{cat}$ is the weight of the loaded catalyst and $M_{MeOH}$ is the molar weight of methanol (32.04 g mol$^{-1}$).

Data reported correspond to the average of the 4 measurements preceding a specific time-on-stream, or to the average of 7 measurements collected during each individual condition when temperature or gas flows were altered. The carbon loss in percent was determined for each experiment according to equation 4 and was found to be always less than 3%.

$$\varepsilon_C = \frac{\dot{n}^{out}_{CO_2} - \dot{n}^{out}_{MeOH} - \dot{n}^{out}_{CO}}{\dot{n}^{in}_{CO_2} + \dot{n}^{in}_{MeOH}} \times 100$$

Specific surface area and pore volume were determined from the sorption isotherm of $N_2$ at 77 K (−196.15° C.). The Brunauer-Emmett-Teller (BET) method was applied for calculating the specific surface area and the volume of gas adsorbed at saturation pressure was used to determine the pore volume.

Scanning transmission electron microscopy (STEM) imaging and energy dispersive X-ray spectroscopy (EDX) measurements were performed using a Talos F200X instrument operated at 200 kV and equipped with an FEI SuperX detector.

The metal composition of the calcined samples was determined by inductively coupled plasma-optical emission spectrometry (ICP-OES) using a Horiba Ultra 2 instrument equipped with photomultiplier tube detector. Prior to analysis, the catalysts were dissolved in aqua regia and the resulting solutions were diluted with twice-distilled water.

Carbon, hydrogen, nitrogen (CHN) were determined by using the standard method in which a solid sample is combusted in a pure oxygen environment above 1173 K. The gases produced are carried by helium and quantified as $CO_2$, $H_2O$, and $N_2$ by a thermal conductivity detector (TCD). The method is based on ASTM D5921.

EXAMPLES

The advantages of the present invention are illustrated in the following examples. However, it is understood that the invention is by no means limited to these specific examples.

Example 1—Catalyst Synthesis

Wet Impregnation (WI)

To obtain 9.5 wt. % $In_2O_3$ and 0.5 wt. % Pd on $ZrO_2$, $In(NO_3)_3 \cdot xH_2O$ (0.821 g, Sigma-Aldrich, 99.99%) and $Pd(NO_3)_2 \cdot xH_2O$ (0.014 g, Sigma-Aldrich, >99.99% metals basis) were placed in a 250-cm$^3$ round-bottom flask and dissolved in deionized water (100 cm$^3$). Then $ZrO_2$ (3.00 g, Alfa Aesar, 99.9% metals basis excluding Hf) was added and the slurry was stirred at room temperature for 30 min. The water was then removed using a rotary evaporator (100 rpm, 313 K, 8 kPa, ca. 90 min) and the sample was further dried in a vacuum oven (1.5 kPa, 323 K, ca. 90 min). Thereafter the sample was calcined at 573 K (2 K min$^{-1}$) for 3 h static air.

Coprecipitation (CP)

To obtain 9.9 wt. % $In_2O_3$ and 0.1 wt. % Pd on $ZrO_2$, $In(NO_3)_3 \cdot xH_2O$ (0.57 g), $Pd(NO_3)_2 \cdot xH_2O$ (0.01 g), and zirconyl nitrate solution (9.67 g, Sigma-Aldrich, 35 wt. % in dilute nitric acid) were placed with 70 cm$^3$ of deionized water in a 250-cm$^3$ round-bottom flask. A 10 wt. % $Na_2CO_3$ solution was prepared by dissolving $Na_2CO_3$ (5.0 g, Merck, >99%) in deionized water in a 50-cm$^3$ volumetric flask. 33.9 cm$^3$ of the $Na_2CO_3$ solution were then added drop-wise to the mixture until a pH of 9.2 was reached. The slurry was aged at room temperature for 60 min, then quenched with deionized water (70 cm$^3$), thereafter the solid was separated by high-pressure filtration and washed with deionized water (3 times, 500 cm$^3$ each time). The solid was then dried in a vacuum oven (1.5 kPa, 323 K, 90 min) and calcined at 573 or 773 K for 3 h (2 K min$^{-1}$) in static air.

Sol-Gel Synthesis (SG)

To obtain 9.5 wt. % $In_2O_3$ and 0.5 wt. % Pd on $ZrO_2$, $In(NO_3)_3 \cdot xH_2O$ (0.55 g), $Pd(NO_3)_2 \cdot xH_2O$ (0.02 g), and zirconyl nitrate solution (9.65 g, 35 wt. % in dilute nitric acid) were placed with nitric acid (0.38 g, Fisher Scientific UK, 65%) and deionized water (3.65 cm$^3$) in a 250-cm$^3$ round-bottom flask and stirred at ambient temperature until dissolution of all solids was observed by eye. A 66.7 wt. % citric acid solution, prepared by dissolving citric acid (1.00 g, Sigma-Aldrich, >98%) in 0.5 cm$^3$ deionized water, was added dropwise to the zirconia mixture. Excess water was removed by evaporation at ambient pressure and 333 K over 3 h, yielding a highly viscous gel. The gel was dried to a powder in a vacuum oven (1.5 kPa, 323 K) and calcined in a tubular oven under a stream (ca. 1 dm$^3_{STP}$ min$^{-1}$) of air at 773 K for 3 h (2 K min$^{-1}$).

Deposition Precipitation (DP)

To obtain 9.0 wt. % $In_2O_3$ and 1 wt. % Pd, $In(NO_3)_3 \cdot xH_2O$ (0.63 g) and $Pd(NO_3)_2 \cdot xH_2O$ (0.05 g) were dissolved in 70 cm$^3$ deionized water in a round bottom flask. $ZrO_2$ (1.80 g) was sieved to have a particle size of ≤125 μm and was added to the metal salts solution. To this mixture, an aqueous $Na_2CO_3$ solution (ca. 10 cm$^3$, 10 wt. %) was added dropwise until a pH of 9.2 was reached at which the slurry was aged for 60 min. The solid was then separated by high-pressure filtration and washed with deionized water (3 times, 500 cm$^3$ each time). Thereafter, it was then dried in a vacuum oven (1.5 kPa, 323 K, 90 min) and calcined either at 773 K for 3 h (2 K min$^{-1}$) in static air.

Co-Precipitation (CP)—Comparative Example

An example of a catalyst containing 0.75 wt. % Pd is as follows: $In(NO_3)_3 \cdot xH_2O$ (3.48 g) and $Pd(NO_3)_2 \cdot xH_2O$ (34.8 mg) were dissolved in deionized water (50 cm$^3$) in a round-bottomed flask. In a second vessel, a $Na_2CO_3$ solution was prepared by hydrolyzing $Na_2CO_3$ (10.0 g) in deionized water (100 cm$^3$). 38.8 cm$^3$ of the $Na_2CO_3$ solution were added dropwise (3 cm$^3$ min$^{-1}$) to the solution of metal nitrates under magnetic stirring at ambient temperature to reach a pH value of 9.2. The resulting slurry was aged for 60 min. After adding deionized water (50 cm³), the precipitate was separated by high-pressure filtration, washed with deionized water (3 times, 500 cm³ each time), dried in a vacuum oven (1.5 kPa, 323 K, 1.5 h), and calcined in static air (573 K, 3 h, 2 K min$^{-1}$).

Wet Impregnation (WI)—Comparative Example

To obtain 10 wt. % $In_2O_3$ on $ZrO_2$, $In(NO_3)_3 \cdot xH_2O$ (0.821 g) were placed in a 250 cm³ round-bottom flask and dissolved in deionized water (100 cm³). Then $ZrO_2$ (3.00 g, Alfa Aesar, 99.9% metals basis excluding Hf) was added and the slurry was stirred at room temperature for 30 min. The water was then removed using a rotary evaporator (100 rpm, 313 K, 8 kPa, ca. 90 min) and the sample was further dried in a vacuum oven (1.5 kPa, 323 K, ca. 90 min). Thereafter the sample was calcined at 573 K (2 K min$^{-1}$) for 3 h static air.

Example 2—Catalyst Testing

Different catalytic system including $Pd/In_2O_3/ZrO_2$ of various Pd loadings were evaluated in a methanol synthesis reaction, the results are given in Table 1.

From this table it can be seen that the presence of palladium improves the STY by comparison to system without palladium, when applied using the correct synthesis method.

the productivity (STY) was around 2.5-times higher when palladium is present. The STY of the bulk oxide ($In_2O_3$) is on the other hand around 4.0-times lower when compared to the STY of the ternary catalytic system of the present invention.

Example 5 Stability of the Catalyst of the Present Invention

FIG. 1 reports the catalytic data collected during a 24-h test to evaluate the stability of the $Pd/In_2O_3/ZrO_2$ catalytic system (0.05 wt. % Pd loading) of the present invention and to compare it with the stability of the corresponding catalytic system devoid of palladium ($In_2O_3/ZrO_2$) and unsupported ($In_2O_3$).

Reaction conditions: 553 K (279.85° C.), 5.0 MPa, 24,000 cm³$_{STP}$ g$_{cat}^{-1}$ h$^{-1}$, 0.1 g of catalyst, molar $H_2$:$CO_2$=4:1.

After an initial STY above 0.30 g$_{MeOH}$ g$_{cat}^{-1}$ h$^{-1}$, a quick rise in the productivity (STY) to reach a STY of 0.36 g$_{MeOH}$ g$_{cat}^{-1}$ h$^{-1}$ has been observed in the first hour of the reaction. Thereafter, the productivity of the catalyst stays unaltered. By comparison with the supported catalyst devoid of palladium, the productivity (STY) was around 1.5-times higher when palladium is present. The STY of the bulk oxide ($In_2O_3$) is on the other hand around 2.5-times lower when compared to the STY of the ternary catalytic system of the present invention.

TABLE 1

Catalyst testing, all samples were measured at 280° C., 5.0 MPa, molar $H_2$:$CO_2$ = 4, WHSV 24,000 cm³$_{STP}$ g$_{cat}^{-1}$ h$^{-1}$.

| Catalyst | Synthesis method | $T_{calcination}$ [K] | Temperature [K] | $Pd_{nominal}$ [wt. %] | $In_2O_{3,nominal}$ [wt. %] | $X_{CO2}$ [%] | $S_{MeOH}$ [%] | $STY_{MeOH}$ [g$_{MeOH}$g$_{cat}^{-1}$h$^{-1}$] |
|---|---|---|---|---|---|---|---|---|
| $Ga_2O_3$—Pd/$SiO_2$[a] | IW | 673 | 523 | 2.0 | 2.6[b] | 13.0 | 70.0 | 0.253 |
| 10 $In_2O_3$/$ZrO_2$ | WI | 573 | 553 | 0.0 | 10.00 | 4.8 | 79.0 | 0.26 |
| Pd—$In_2O_3$ | CP | 573 | 553[a] | 0.75 | 99.25 | 11.5 | 78.0 | 0.66 |
| 9.5/0.5 $In_2O_3$—Pd/$ZrO_2$ | WI | 573 | 553 | 0.5 | 9.50 | 6.9 | 78.8 | 0.37 |
| 9.9/0.1 $In_2O_3$—Pd/$ZrO_2$ | CP | 573 | 553 | 0.1 | 9.90 | 0.0 | — | 0.00 |
| 9.5/0.5 $In_2O_3$—Pd/$ZrO_2$ | SG | 573 | 553 | 0.5 | 9.50 | 1.3 | 98.6 | 0.09 |
| 9.9/0.1 $In_2O_3$—Pd/$ZrO_2$ | DP | 573 | 553 | 0.1 | 9.90 | 5.2 | 75.6 | 0.27 |
| 9.9/0.1 $In_2O_3$—Pd/$ZrO_2$ | DP | 773 | 553 | 0.1 | 9.90 | 6.1 | 77.8 | 0.33 |
| 9.0/1.0 $In_2O_3$—Pd/$ZrO_2$ | DP | 553 | 553 | 1.0 | 9.00 | 12.1 | 75.9 | 0.63 |
| 9.0/1.0 $In_2O_3$—Pd/$ZrO_2$ | DP | 773 | 553 | 1.0 | 9.00 | 14.0 | 73.2 | 0.70 |
| 9.0/1.0 $In_2O_3$—Pd/$ZrO_2$ | WI | 773 | 553 | 1.0 | 9.00 | 11.2 | 81.3 | 0.63 |

[a]Conditions: molar $H_2$:$CO_2$ = 3, 3.0 MPa, space velocity = 7800 h$^{-1}$. IW = incipient wetness, Reference: S. E. Collins, et al. Catal. Lett. 2005, 103, 83-88.
[b]$Ga_2O_3$.

Figure 2:
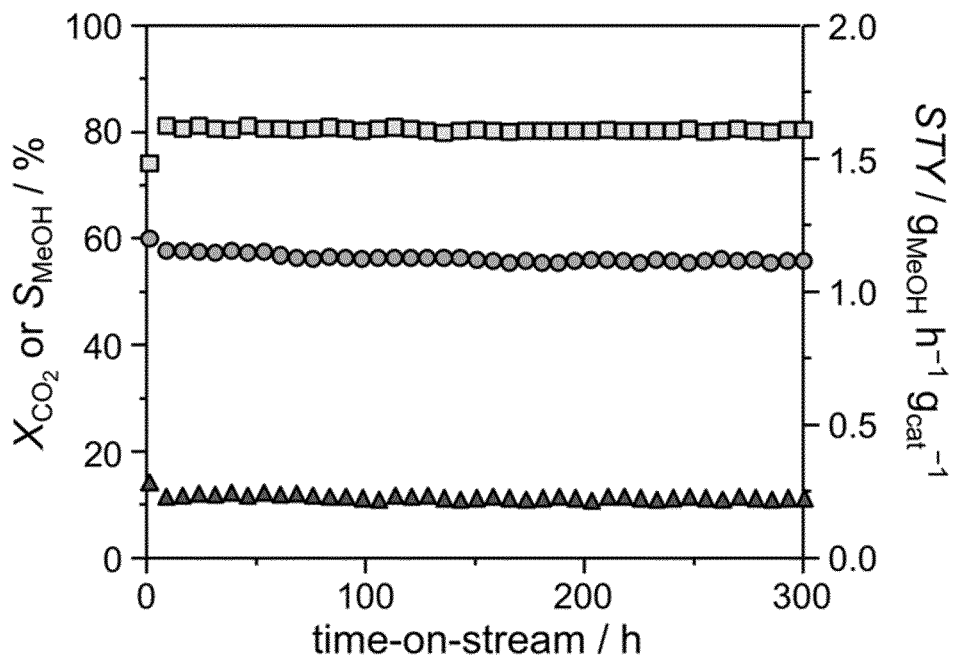
FIG. 2 demonstrates the evolution of conversion, selectivity, and STY over 0.05 wt. % palladium and 9.95 wt. % indium oxide on zirconia. Conditions: WHSV=48,000, molar $H_2:CO_2$=4, 5.0 MPa, 553 K, catalyst prepared via deposition precipitation.
Figure 3:
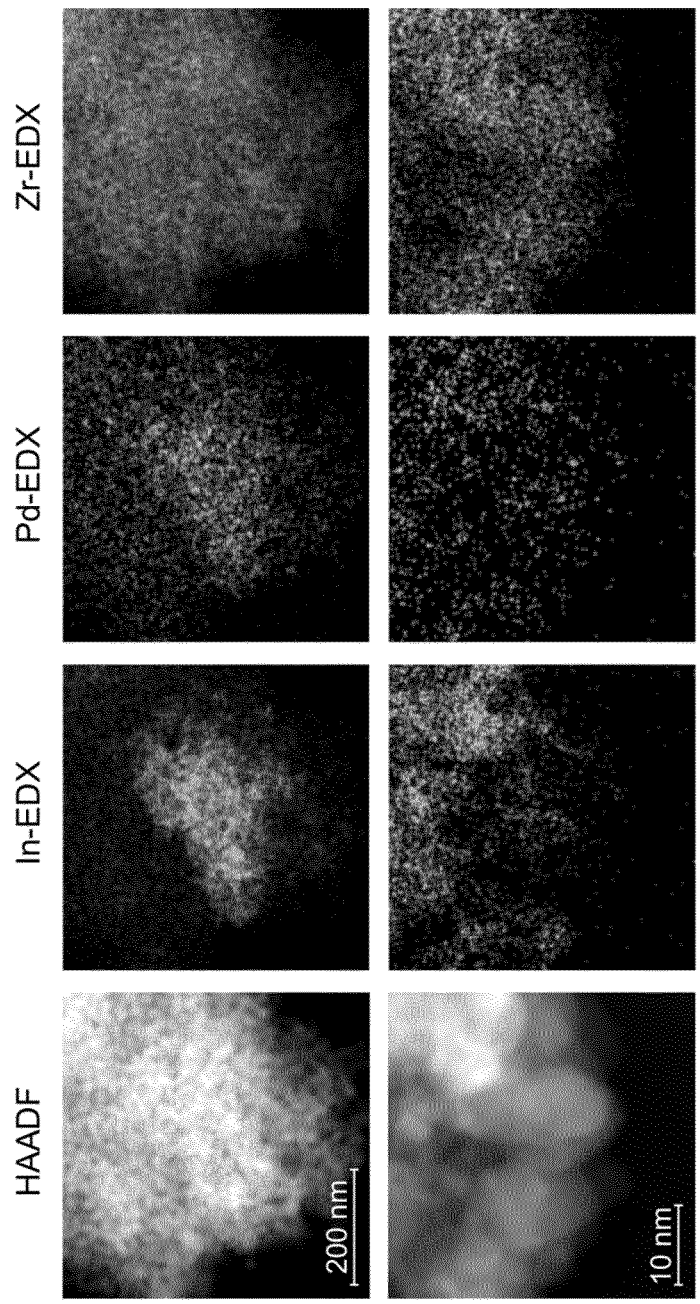
FIG. 3 shows scanning transmission electron microscopy coupled to energy dispersive X-ray mapping (STEM-EDX) images of the same sample as in FIG. 2 at low (top row) and high (bottom row) magnification.
Figure 4:
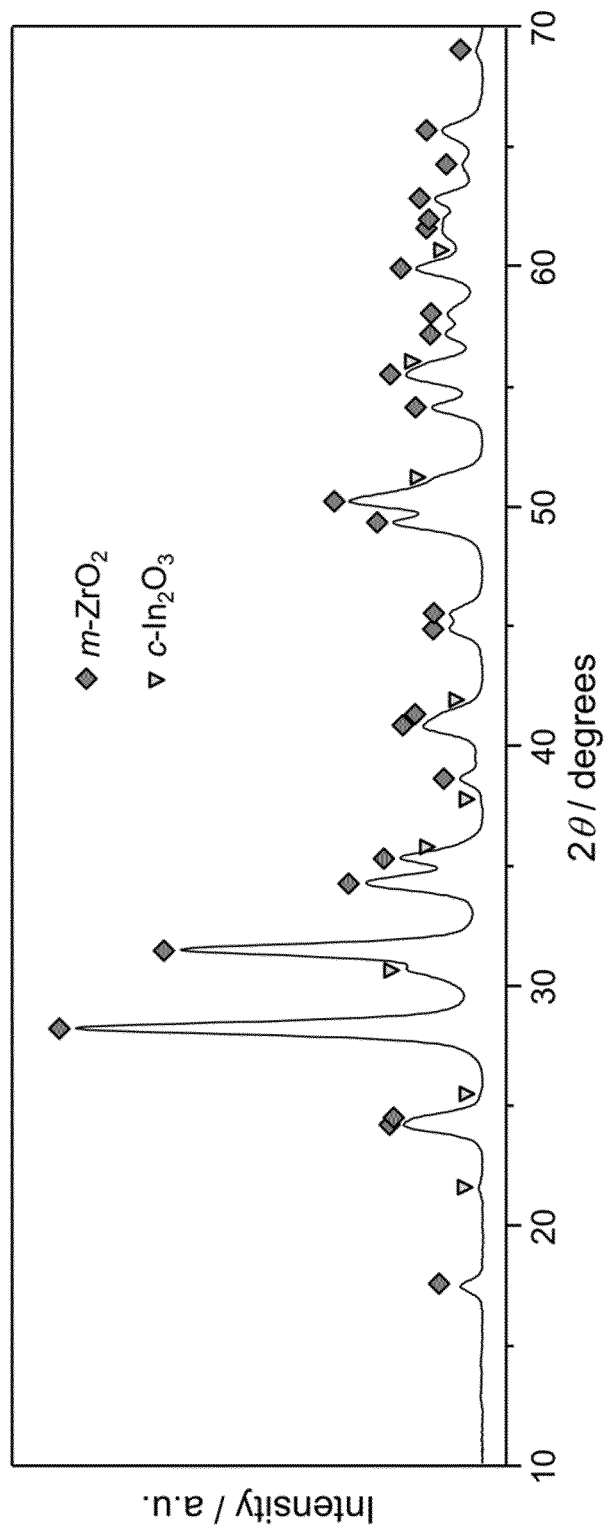
FIG. 4 shows the power X-ray diffraction pattern of the same sample as in FIG. 2, in which the reflections specific to $In_2O_3$ and $ZrO_2$ phases are marked.

Example 4 Conversion of Carbon Dioxide, Selectivity Towards Methanol, and the Resulting $STY_{MeOH}$ Over Time FIG. 2 reports the catalytic data collected during a 300-h test to evaluate the selectivity in methanol ($S_{MeOH}$) and the conversion of $CO_2$ achieved by the $Pd/In_2O_3/ZrO_2$ catalytic system (1.0 wt. % Pd loading and 9.0 wt. % $In_2O_3$ loading) of the present invention. The tests was performed at 553.15 K (280° C.), 5.0 MPa, molar $H_2$:$CO_2$=4, WHSV=48,000 cm³$_{STP}$ g$_{cat}^{-1}$ h$^{-1}$, 0.1 g of catalyst.

It is thus demonstrated that the selectivity in methanol is slightly below 80% (79.9%) and stays unaltered over 300 hours on stream.

Similarly, the conversion in $CO_2$ is slightly above 10% (10.1%) and does not change over 300 hours on stream.

The space-time yield of methanol ($STY_{MeOH}$) for the same test is shown to be stable at 1.10 g$_{MeOH}$ g$_{cat}^{-1}$ h$^{-1}$. By comparison with the supported catalyst devoid of palladium,

The invention claimed is:

1. Supported catalyst for use in a process for the synthesis of methanol, characterized in that the supported catalyst comprises indium oxide in the form of $In_2O_3$ and at least one noble metal being palladium, Pd, wherein both indium oxide and at least one noble metal are deposited on a support characterized in that the supported catalyst is a calcined supported catalyst comprising:

from 0.01 to 10.0 wt. % of palladium and zirconium dioxide ($ZrO_2$) in an amount of at least 50 wt. % on the total weight of said supported catalyst;

wherein the average particle size of the noble metal phase is less than 5 nm as determined by STEM-EDX or the average crystal size of $In_2O_3$ is less than 20 nm, as determined by XRD.

2. The supported catalyst according to claim 1, characterized in that the supported catalyst comprises from 0.5 wt. % to 2.0 wt. %. of palladium based on the total weight of said supported catalyst.

3. The supported catalyst according to claim 1, characterized in that the support comprises zirconium dioxide ($ZrO_2$) in an amount of at least 80 wt. %, based on the total weight of said supported catalyst.

4. The supported catalyst according to claim 1, characterized in that the support comprises zirconium dioxide ($ZrO_2$) in an amount of at least 90 wt. % based on the total weight of said supported catalyst.

5. The supported catalyst according to claim 1, characterized in that the supported catalyst is a calcined supported catalyst and in that the indium oxide content in the form of $In_2O_3$ ranges from 1 to 20% by weight based on the total weight of said supported catalyst.

6. The supported catalyst according to claim 1, characterized in that the supported catalyst is a calcined supported catalyst and in that the indium oxide content in the form of $In_2O_3$ ranges from 5 to 15% by weight based on the total weight of said supported catalyst.

7. The supported catalyst according to claim 1, characterized in that the supported catalyst is a calcined supported catalyst.

8. The supported catalyst according to claim 1, characterized in that the supported catalyst is a calcined supported catalyst and has a surface area in the range of about 30 $m^2$ $g^{-1}$ to about 200 $m^2$ $g^{-1}$, as determined according to $N_2$ sorption analysis according to ASTM D3663-03.

9. A method to prepare a supported catalyst according claim 1 characterized in that the supported catalyst is prepared by impregnation or by deposition precipitation.

10. A method according to claim 9, characterized in that the supported catalyst is a calcined supported catalyst, and in that the method comprises a step of calcination of the supported catalyst performed at a temperature of at least 473 K (199.85° C.).

11. The method according to claim 9, characterized in that the supported catalyst is a calcined supported catalyst, and in that the method comprises a step of calcination of the supported catalyst performed at a temperature of at least 573 K (299.85° C.).

12. Process for methanol synthesis comprising:
providing a feed stream comprising hydrogen and carbon oxides selected from carbon dioxide or a mixture of carbon dioxide and carbon monoxide, wherein carbon dioxide represents from 1 to 50 mol % of the total molar content of the feed stream, carbon monoxide is contained from 0 to 85 mol % of the total molar content, and $H_2$ is comprised from 5 to 99 mol % of the total molar content of the feed stream;
providing a catalyst according to claim 1;
putting in contact said feed stream with said catalyst at a reaction temperature of at least 373 K (99.85° C.) and under a pressure of at least 0.5 MPa; and
recovering the methanol from the effluents by a separation process;
wherein the feed stream is put in contact with the supported catalyst at a weight hourly space velocity ranging from 1,000 to 60,000 $cm3_{STP}$ $g_{cal}$ $h^{-1}$.

13. Process according to claim 12, characterized in that: the reaction temperature is at least 463 K (189.85° C.).

14. Process according to claim 12, characterized in that the feed stream is put in contact with the supported catalyst at a weight hourly space velocity ranging from 10,000 to 60,00$cm^3_{STP}$ $g_{cal}$ $h^{-1}$.

15. Process according to claim 12, characterized in that the feed stream is put in contact with the supported catalyst at a weight hourly space velocity ranging from 24,000 to 48,000 $cm^3_{STP}$ $g_{cal}$ $h^{-1}$.

16. Process according to claim 12, characterized in that the molar ratio of hydrogen to carbon dioxide in the feed stream is at least 1:1.

17. Process according to claim 12, characterized in that the molar ratio of hydrogen to carbon dioxide in the feed stream is at least 3:1.

18. Process according to claim 12, characterized in that prior to reaction the supported catalyst is activated in situ by raising the temperature to at least 553 K (279.85° C.) in a flow of a gas feed stream for activation selected from inert gases, hydrogen, carbon monoxide, carbon dioxide or mixture thereof.

* * * * *

UNITED STATES PATENT AND TRADEMARK OFFICE
CERTIFICATE OF CORRECTION

PATENT NO. : 11,491,468 B2
APPLICATION NO. : 17/272872
DATED : November 8, 2022
INVENTOR(S) : Stewart et al.

It is certified that error appears in the above-identified patent and that said Letters Patent is hereby corrected as shown below:

In the Claims

Claim 14, Column 16, Line 24:
"60,00cm$^3_{STP}$ g$_{cal}$ h$^{-1}$."
Should read:
"60,000 cm$^3_{STP}$ g$_{cal}$ h$^{-1}$."

Signed and Sealed this
Thirty-first Day of January, 2023

Katherine Kelly Vidal
*Director of the United States Patent and Trademark Office*